(12) United States Patent
Richter et al.

(10) Patent No.: US 12,140,654 B2
(45) Date of Patent: Nov. 12, 2024

(54) COMPUTER-IMPLEMENTED METHOD FOR DETERMINING A DYNAMIC CONTRAST-ENHANCED MAGNETIC RESONANCE DATA SET, MAGNETIC RESONANCE IMAGING DEVICE, COMPUTER PROGRAM AND ELECTRONICALLY READABLE STORAGE MEDIUM

(71) Applicant: Siemens Healthcare AG, Forccheim (DE)

(72) Inventors: Julian Richter, Hessdorf (DE); Manuel Stich, Schwandorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 51 days.

(21) Appl. No.: 17/967,191

(22) Filed: Oct. 17, 2022

(65) Prior Publication Data
US 2023/0117041 A1   Apr. 20, 2023

(30) Foreign Application Priority Data
Oct. 19, 2021   (EP) ..................................... 21203544

(51) Int. Cl.
*G01R 33/561*   (2006.01)
*A61B 5/055*   (2006.01)
(Continued)

(52) U.S. Cl.
CPC .......... *G01R 33/5611* (2013.01); *A61B 5/055* (2013.01); *G01R 33/5601* (2013.01); *G01R 33/5619* (2013.01); *G01R 33/4818* (2013.01)

(58) Field of Classification Search
CPC ............ G01R 33/5611; G01R 33/4818; G01R 33/56518; G01R 33/56572;
(Continued)

(56) References Cited

U.S. PATENT DOCUMENTS

| 2018/0164395 A1* | 6/2018 | Setsompop ............ H04B 1/717 |
| 2023/0089051 A1* | 3/2023 | Richter .............. G01R 33/4826 |

OTHER PUBLICATIONS

Breuer, Felix A. et al. "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.
(Continued)

*Primary Examiner* — Rishi R Patel
(74) *Attorney, Agent, or Firm* — Harness, Dickey & Pierce, P.L.C.

(57) ABSTRACT

A plurality of reception coils are used to acquire magnetic resonance signals using parallel imaging and a k-space acquisition scheme, in which alternatingly the central region and one of the peripheral k-space portions are imaged in acquisition steps of a pair, such that after a partition number of such pairs, the whole k-space to be acquired has been imaged and a sliding reconstruction window can be applied to reconstruct an additional magnetic resonance image after each acquisition of such a pair. A time series of magnetic resonance images forming the magnetic resonance data set is then reconstructed from the magnetic resonance signals and sensitivity information regarding the plurality of reception coils by using the sliding reconstruction window and a reconstruction technique for undersampled magnetic resonance data. The k-space trajectories for each acquisition step are chosen to allow controlled aliasing in all three spatial dimensions including the readout direction.

13 Claims, 3 Drawing Sheets

(51) Int. Cl.
*G01R 33/48* (2006.01)
*G01R 33/56* (2006.01)

(58) Field of Classification Search
CPC ............ G01R 33/5601; G01R 33/5619; G01R 33/5608; A61B 5/055
See application file for complete search history.

(56) References Cited

OTHER PUBLICATIONS

Richter, J.A.J., Wech, T. et al: "Free-breathing self-gated 4D lung MRI using wave-CAIPI". in: Magn Reson Med. 2020; 84: 3223-3233. DOI: 10.1002/mrm.28383.

Richter, A. J. Julian et al: "Accelerated aortic 4D flow MRI with wave-CAIPI"; Magnetic Resonance in Medicine; vol. 85, No. 5, Nov. 24, 2020 (Nov. 24, 2020), pp. 2595-2607, XP055900733.

Bilgic, Berkin et al. "Wave-CAIPI for Highly Accelerated 3D Imaging" Magnetic Resonance in Medicine, vol. 73, No. 6, pp. 2152-2162, Jun. 2015 (First published: Jul. 1, 2014) // https://doi.org/10.1002/mrm.25347//XP055645454.

Hamilton, Jesse et al: "Recent advances in parallel imaging for MRI"; Progress in Nuclear Magnetic Resonance Spectroscopy; vol. 101, May 2, 2017 (May 2, 2017), pp. 71-95, XP085170513.

Song, Ting et al:"Optimal k-Space Sampling for Dynamic Contrast-Enhanced MRI with an Application to MR Renography", in: Magnetic Resonance in Medicine; vol. 61, No. 5, Feb. 19, 2009 (Feb. 19, 2009), pp. 1242-1248 , XP055900748; DOI: 10.1002/mrm.21901.

Eirich, P. et al: "Cardiac real-time MRI using a pre-emphasized spiral acquisition based on the gradient system transfer function", in: Magnetic Resonance in Medicine 85(5):2747-2760 (2021). DOI:10.1002/mrm.28621.

Stich, M. et al. "Field Camera versus Phantom-based Measurement of the Gradient System Transfer Function (GSTF) with dwell time compensation", Magn Reson Med. 2020;71:125-131.

Polak, D. et. al., "Highly-accelerated volumetric brain examination using optimized wave-CAIPI encoding," J. Magn. Reson. Imaging, vol. 50, No. 3, pp. 961-974, 2019.

Griswold, Mark A. et al. "Generalized Autocalibrating Partially Parallel Acquisitions (GRAPPA)" Magnetic Resonance in Medicine, vol. 47, pp. 1202-1210, 2002 // DOI: 10.1002/mrm.10171.

Othman, E. Ahmed et al: "Feasibility of CAIPIRINHA-Dixon-TWIST-VIBE for dynamic contrast-enhanced MRI of the prostate"; European Journal of Radiology; vol. 84, No. 11, Nov. 1, 2015 (Nov. 1, 2015), pp. 2110-2116, XP055900912.

Michaely, J. Henrik et al: "CAIPIRINHA-Dixon-TWIST (CDT)-Volume Interpolated Breath-Hold Examination (VIBE)"; Investigative Radiology, vol. 48, No. 8, Aug. 1, 2013 (Aug. 1, 2013) , pp. 590-597, XP055900691.

Otazo, Ricardo et al: "Low-rank plus sparse matrix decomposition for accelerated dynamic MRI with separation of background and dynamic components"; Magnetic Resonance in Medicine; vol. 73, No. 3, pp. 1125-1136, 2015.

Petrov A.Y. et al.:"Improving temporal resolution in fMRI using a 3D spiral acquisition and low rank plus sparse (L+S) reconstruction" in: NeuroImage 157 (2017). DOI:10.1016/j.neuroimage.2017.06.004.

* cited by examiner

COMPUTER-IMPLEMENTED METHOD FOR DETERMINING A DYNAMIC CONTRAST-ENHANCED MAGNETIC RESONANCE DATA SET, MAGNETIC RESONANCE IMAGING DEVICE, COMPUTER PROGRAM AND ELECTRONICALLY READABLE STORAGE MEDIUM

CROSS-REFERENCE TO RELATED APPLICATION(S)

The present application claims priority under 35 U.S.C. § 119 to European Patent Application No. 21203544.8, filed Oct. 19, 2021, the entire contents of which are incorporated herein by reference.

FIELD

One or more example embodiments of the present invention concern a computer-implemented method for determining a dynamic contrast-enhanced magnetic resonance data set of an imaging region of a patient, wherein the k-space to be acquired is divided into a central region comprising the k-space center and a peripheral region surrounding the central region, and wherein the peripheral region comprises a partitioning number of peripheral k-space portions, comprising the steps of
using a plurality of reception coils to acquire magnetic resonance signals using parallel imaging and a k-space acquisition scheme, in which alternatingly the central region and one of the peripheral k-space portions, the peripheral k-space portion being chosen according to a pre-determined order, are imaged in acquisitions steps of a pair, such that, after the partition number of such pairs, the whole k-space to be acquired has been imaged and a sliding reconstruction window can be applied to reconstruct an additional magnetic resonance image after each acquisition of such a pair, wherein during acquisition undersampling in at least two k-space directions is performed,
reconstructing a time series of magnetic resonance images forming the magnetic resonance data set from the magnetic resonance signals and sensitivity information regarding the plurality of reception coils by using the sliding reconstruction window and a reconstruction technique for undersampled magnetic resonance data.

One or more example embodiments of the present invention further concern a magnetic resonance imaging device, a computer program and an electronically readable storage medium.

BACKGROUND

Magnetic resonance imaging (MRI) has become an established modality in medical imaging. For angiography in various body regions, dynamic contrast-enhanced MRI (DCE-MRI) may be used. Examples include imaging of the renal arteries or the carotid arteries. To accurately assess vessel constitution and blood flow, in particular regarding irregularities, three-dimensional acquisitions are performed, which should be of a high spatial and temporal resolution. The acquisition time is limited and governed by the evolution of the contrast agent along the vessels. Hence, a compromise between temporal and spatial resolution has to be found.

A known technique for DCE-MRI is based on the so-called TWIST sampling scheme (time-resolved angiography with stochastic trajectories, see the article by Ting Song et al., "Optimal k-Space Sampling for Dynamic Contrast-Enhanced MRI with an Application to MR Renography", Magnetic Resonance in Medicine 61:1242-1248 (2009)). Here, the k-space to be acquired is divided into a central region and a peripheral region, which, again, is divided into several (n, partitioning number) peripheral k-space portions. In the TWIST technique, these peripheral k-space portions, in concrete embodiments subsets of k-space lines in the peripheral region, are usually each spread over the peripheral region. An order of the peripheral k-space portions is defined. During acquisition, pairs of the central region (A) and one of the peripheral k-space portions (B1 . . . Bn) are acquired, the latter chosen according to the pre-determined order. For example, for partitioning number n=3, the acquisition order may be (A, B1), (A, B2), (A, B3), (A, B1), (A, B2), . . . Hence, after each n acquisitions, the k-space has been fully sampled. In each acquisition step for a pair, that is for A and the Bi, i=1 . . . n, Cartesian k-space trajectories are employed.

During reconstruction, a sliding reconstruction window is used in order to reconstruct several magnetic resonance images for different time frames, wherein the sliding reconstruction window covers n consecutively acquired pairs, that is, magnetic resonance signals for the whole k-space to be acquired. Hence, consecutive magnetic resonance images are not disjunct on the magnetic resonance signals (k-space data) level. However, the temporal resolution is considerably increased compared to simply acquiring consecutive images.

To further increase the temporal resolution, undersampling and parallel imaging techniques may be combined with TWIST imaging.

Generally, undersampling may result in aliasing artefacts in the spatial domain. Hence, dynamic imaging and reconstruction approaches have been proposed using parallel imaging techniques, in particular to control aliasing. For example, GRAPPA (see M. A. Griswold et al, "Generalized autocalibrating partially parallel acquisitions (GRAPPA)", Magnetic Resonance in Medicine 47(6):1202-1210 (2002)) or controlled aliasing in parallel imaging results in higher acceleration (CAIPIRINHA, see F. A. Breuer et al, "Controlled Aliasing in Parallel Imaging Results in Higher Acceleration (CAIPIRINHA) for Multi-Slice Imaging", Magnetic Resonance in Medicine 53:684-691 (2005)) may be used. For example, CAIPIRINHA improves reconstruction quality for multislice acquisitions by modulating the phase of the simultaneously excited slices. This modification incurs interslice shifts in the phase encoding direction between aliasing image slices, thereby increasing the variation in the coil sensitivity profiles across the slices to improve slice dealiasing. The application of interslice shifts to three-dimensional imaging forms the basis of 2D-CAIPIRINHA, wherein the encoding strategy in the phase encoding direction and the slice select direction is modified to shift the spatial aliasing pattern to reduce aliasing and better exploit the coil sensitivity variation.

However, parallel imaging techniques inherently increase the noise in the reconstructed magnetic resonance images. The degree of noise enhancement may be quantified by the so-called g-factor (geometry factor). High degrees of undersampling along the Cartesian k-space trajectory lead to large g-factors, signifying considerable noise enhancement.

Regarding reconstruction techniques, in an article by Ricardo Otazo et al., "Low-rank plus sparse matrix decomposition for accelerated dynamic MRI with separation of background and dynamic components", Magnetic Resonance in Medicine 73 (2015), pages 1125-1136, a new model for undersampled dynamic magnetic resonance data was proposed. This approach assumes that the dynamic MRI data, represented as a space-time matrix M, is a linear superposition of a low-rank matrix L and a sparse matrix S, wherein L represents highly spatially and temporally correlated elements, such as the image background, while S captures dynamic information that is sparse in an appropriate transform domain. Hence, this reconstruction technique is also known as L+S technique.

SUMMARY

It is an object of one or more example embodiments of the present invention to, in particular significantly, increase image quality and/or temporal and/or spatial resolution in DCE-MRI.

At least this object is achieved by providing a method according to one or more example embodiments of the present invention, a magnetic resonance device according to one or more example embodiments of the present invention, a computer program according to one or more example embodiments of the present invention, and an electronically readable storage medium according to one or more example embodiments of the present invention.

In a method as initially described, according to one or more example embodiments of the present invention, the k-space trajectories for each acquisition step are chosen to allow controlled aliasing in all three spatial dimensions including the readout direction.

One or more example embodiments of the present invention are based on a technique dividing the k-space to be acquired into a central region and a peripheral region, wherein the peripheral region is further subdivided into peripheral k-space portions to be acquired alternatingly with the central portion in a pre-determined order, such that, by using a sliding reconstruction window, for each time step, the oldest acquired magnetic resonance signals of the central region and a certain peripheral k-space portion are replaced by the more recently acquired magnetic resonance signals of the central region and the certain peripheral k-space portion. A sequence unit in a control device may control the acquisition components of a magnetic resonance device to acquire magnetic resonance signals. In all the acquisition steps for the central region and the peripheral k-space portions, certain k-space trajectories, implemented by gradient coils of a gradient system of the magnetic resonance device, are used to acquire the respective magnetic resonance signals. Here, an embodiment of the present invention proposes to use a 3D k-space trajectory which allows controlled aliasing in all three dimensions and hence can use the whole coil sensitivity information. That is, in particular, a three-dimensional sensitivity distribution of the reception coils is used as the sensitivity information during reconstruction.

Preferably, a TWIST sampling scheme is used to stochastically define the peripheral k-space portions. It is referred to the above-cited article by Ting Song et al. In particular, in preferred embodiments, the division of the k-space may be performed in a plane perpendicular to the readout direction, that is, in a plane spanned by the two phase encoding directions (ky, kz). In a conventional approach, the regions and portions would then comprise k-space lines in the readout direction (kx), while in the current invention, three-dimensional sub-trajectories replacing the conventional k-space lines and allowing to exploit the full three-dimensional sensitivity information are used.

In especially preferred embodiments, for each acquisition step, the k-space trajectory is defined by a wave-encoded 3D gradient echo magnetic resonance sequence using sinusoidal gradient pulses with a quarter cycle phase shift in the phase encoding directions. Such wave-encoding has already been proposed for so called wave-CAIPI approaches and can easily be transferred to and employed in the method of an embodiment of the present invention, since it only requires adding additional gradient pulses and does not affect phase encoding. The sinusoidal gradient wave oscillations lead to corkscrew-shaped readout trajectories in 3D k-space (instead of k-space lines). The additional wave-encoding leads to wide voxel spreading of aliased image voxels in all three spatial dimensions, including the readout direction kx (often also called frequency encoding direction), which is not used for acceleration in Cartesian imaging. In the image domain, the additional phase deposition results in voxel-spreading along the readout direction which varies linearly as a function of the spatial y and z position. A well distributed aliasing pattern is created, allowing use of the whole three-dimensional sensitivity distribution in reconstruction. Hence, undersampling artifacts can be more efficiently corrected. The resulting g-factor is lower, such that reconstructed magnetic resonance images of the magnetic resonance data set show lower noise enhancement compared to the conventional Cartesian technique. The wave-CAIPI approach and its effect on the g-factor is, for example, described in B. Bilgic et al, "Wave-CAIPI for Highly Accelerated 3D Imaging", Magnetic Resonance in Medicine 73:6 (2015), J. A. J. Richter et al, "Accelerated aortic 4D flow MRI with wave-CAIPI", Magnetic Resonance in Medicine 85:2595-2607 (2021), J. A. J. Richter et al, "Free-breathing self-gated 4D lung MRI using wave-CAIPI", Magnetic Resonance in Medicine 84: 3223-3233 (2020), and D. Polak et al, "Highly-accelerated volumetric brain examination using optimized wave-CAIPI encoding", Magnetic Resonance in Medicine 50(3):961-974 (2019).

In summary, an accelerated setup is proposed for DCE-MRI, using a k-space trajectory allowing to take coil sensitivity information from all three dimensions into account, in particular a wave-encoded 3D k-space trajectory. 3D k-space trajectories inherently yield higher signal-to-noise-ratio than 2D techniques, which may be traded for an improved spatial and/or temporal resolution. The 3D k-space trajectory provides increased potential for acceleration with parallel imaging or compressed sensing, due to the possibility to exploit the full three-dimensional coil sensitivity information, that is, the three-dimensional sensitivity distribution of the reception coils. Wave-encoding leads to lower noise enhancement in highly undersampled magnetic resonance data sets. Hence, the proposed technique bears potential to significantly increase temporal and/or spatial resolution in DCE-MRI.

In an especially advantageous embodiment of the current invention, a low rank plus sparse (L+S) reconstruction technique is used as the reconstruction technique, wherein the dynamic magnetic resonance data as a space-time matrix is assumed as a linear superposition of a highly spatially and temporarily correlated image background matrix and a sparse dynamic information matrix. The L+S image reconstruction technique has proven very effective in dynamic MRI applications. The L+S model takes spatial correlation in 3D images into account, but also temporal correlations in dynamic image series, which facilitates reconstruction of highly undersampled magnetic resonance data sets. In particular in DCE-MRI, the L+S compressed sensing model is promising, since the magnetic resonance image series typically shows only little variation in signal intensities, such that the image series could be efficiently represented by a low-rank background (L-matrix) and a temporally varying sparse component (S-matrix). If L+S compressed sensing reconstruction techniques are used instead of, for example, GRAPPA and/or SMS, lower noise in undersampled images results, providing the possibility for higher acceleration without compromising image quality. For example, the different time steps in TWIST imaging, that is the individual magnetic resonance images, differ only marginally and are therefore highly correlated in the temporal dimension. These correlations can be leveraged to achieve reconstructions of high quality. Generally, the reconstruction if further aided by the incoherent appearance of aliasing caused by the wave-encoding, providing a synergistic effect.

That is, while conventional image reconstruction processes each time step, in particular each TWIST phase, individually, the dynamic compressed sensing L+S model, i.e., including temporal regularization, is efficient in the reconstruction of dynamic DCE-MRI data, as, for example, also described in an article by R. Otazo et al., "Low-rank plus sparse matrix decomposition for accelerated dynamic MRI with separation of background and dynamic components", Magnetic Resonance in Medicine 73:3 (2015). By employing the L+S model, the inherent temporal correlations of the individual phases, which are defined by the sliding reconstruction window, are exploited to arrive at high quality image reconstructions. In the inventive approach, image reconstruction is further facilitated by the wave-encoding technique, since wave-encoding leads to incoherent aliasing in all dimensions, which is beneficial for general compressed sensing reconstructions. Combining the wave-encoding technique and the L+S compressed sensing model, higher acquisition acceleration is possible, leading to increased temporal resolutions in DCE-MRI.

Regarding undersampling, as known from the TWIST sampling scheme and approach, two sampling parameters may be defined and optimized accordingly, namely pA, which specifies the proportion of the central region A regarding the k-space to be acquired, and pB, which determines the density of sampling of the peripheral region B. Hence, TWIST offers two independent ways to improve the temporal resolution, that is by lowering pA (reducing the size of the central region) and by lowering pB (sampling the peripheral region more sparsely. Both approaches have certain tradeoffs: lowering pA will decrease the amount of low spatial frequency information, while lowering pB will decrease the fidelity of small features and fine image textures.

In preferred embodiments, the gradient system transfer function may be used to correct for inaccuracies during reconstruction. The challenges regarding the reconstruction of non-Cartesian k-space can be efficiently overcome by using the Gradient System Transfer Function (GSTF) to correct for gradient inaccuracies. Since gradient errors may lead to severe image artifacts, these challenges regarding the reconstruction of non-Cartesian k-space can be efficiently overcome by using the so-called gradient system transfer function (GSTF) to correct for gradient inaccuracies and hence further increase image quality and/or the option for increasing resolution. GSTF-based correction approaches are, for example, described in the already cited articles by J. R. J. Richter regarding wave-CAIPI, and in M. Stich et al, "Field camera versus phantom-based measurement of the gradient system transfer function (GSTF) with dwell time compensation", Magnetic Resonance Imaging 71:125-131 (2020) and P. Eirich et al., "Cardiac real-time MRI using a pre-emphasized spiral acquisition based on the gradient system transfer function", Magnetic Resonance in Medicine 85(5):2747-2760 (2021).

One or more example embodiments of the present invention further concern a magnetic resonance imaging device, comprising a control device configured to perform a method according to one or more example embodiments of the present invention. All comments and remarks regarding the method according to the present invention analogously apply to the magnetic resonance imaging device according to the present invention, such that the same advantages can be achieved.

The control device may comprise at least one processor and at least one storage device. As principally known in the state of the art, the control device may further, to acquire magnetic resonance signals, comprise a sequence unit, in particular controlling operation of a gradient system and at least one radio frequency system, in particular comprising the plurality of reception coils. The control device may further comprise a reconstruction unit for reconstructing the magnetic resonance images from the magnetic resonance signals acquired using the sequence unit, which is configured to use a k-space trajectory allowing controlled aliasing in all three spatial dimensions including the readout direction, in particular a wave-encoded 3D gradient echo trajectory.

A computer program according to one or more example embodiments of the present invention can be directly loaded into a control device of a magnetic resonance imaging device and comprises at least one processor or other processing circuitry (or, alternatively, means) to perform the steps of a method according to one or more example embodiments of the present invention when the computer program is executed on the control device. The computer program may be stored on an electronically readable storage medium according to one or more example embodiments of the present invention, which thus comprises control information comprising a computer program according to one or more example embodiments of the present invention such that when the electronically readable storage medium is used in a control device of a magnetic resonance device, the control device performs the steps of a method according to one or more example embodiments of the present invention. The electronically readable storage medium is preferably a non-transitional medium, for example a CD-ROM.

BRIEF DESCRIPTION OF THE DRAWINGS

Other objects and features of the present invention will become apparent from the following detailed description considered in conjunction with the accompanying drawings. The drawings, however, are only principle sketches designed solely for the purpose of illustration and do not limit the present invention. The drawings show:

FIG. 1 a flow chart of a method according to one or more example embodiments of the present invention, FIG. 2 a drawing explaining the definition of the central region and the peripheral region, FIG. 3 a possible definition of peripheral k-space portions, FIG. 4 a TWIST sampling scheme with a sliding reconstruction window, FIG. 5 a pulse sequence diagram for an acquisition step employing wave-encoding, and FIG. 6 a magnetic resonance imaging device according to one or more example embodiments of the present invention.

DETAILED DESCRIPTION

Figure 1:
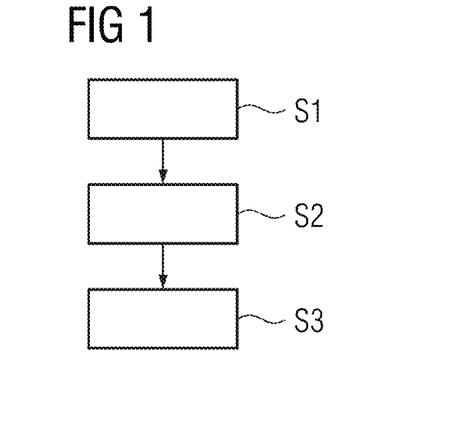

In FIG. 1, an embodiment of a method for operating a magnetic resonance device for determining a dynamic contrast-enhanced magnetic resonance dataset, comprising a time series of magnetic resonance images, is described. For example, angiography of the renal or carotid arteries can be carried out.

Figure 2:
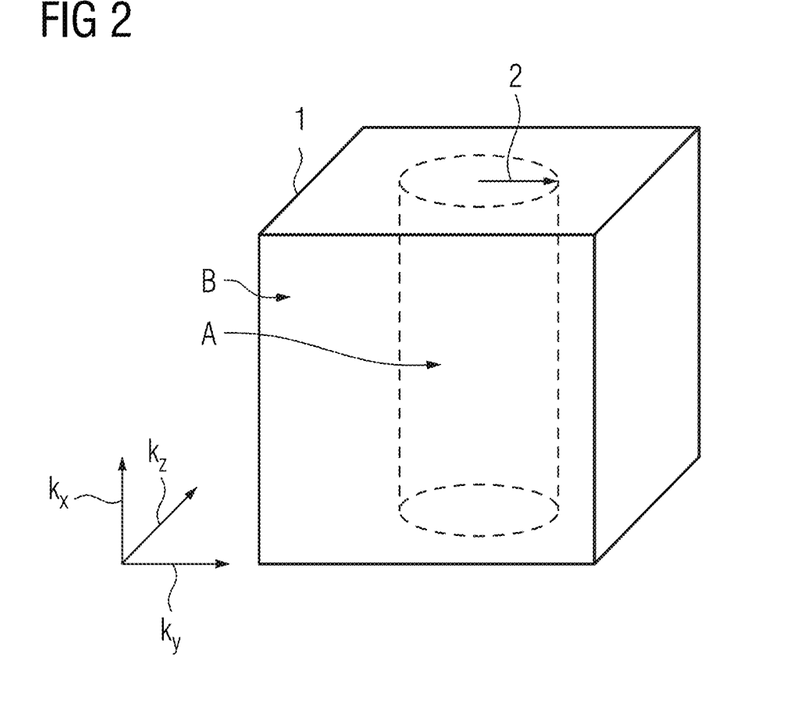

In a step S1, the k-space 1 to be acquired is divided into two regions A, B, as shown in FIG. 2, for example dependent on a chosen proportion of the central region A with respect to the k-space 1, in this case definable by the radius 2, also see the parameter pA as described above. The central region A comprises the k-space center. The outer or peripheral region B surrounds the region A.

Figure 3:
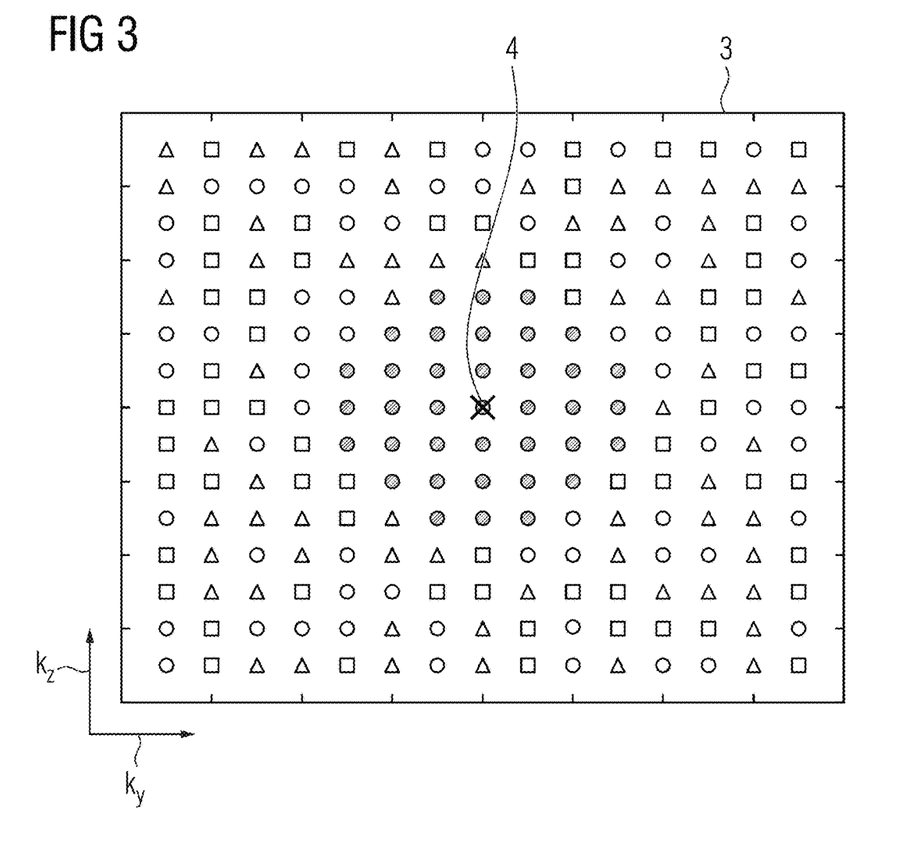

FIG. 3 shows trajectory starting points in the phase encoding plane 3 (ky and kz-directions). The k-space center 4 is accordingly marked, as are the starting points belonging to the central region A as filled circles. In the TWIST sampling scheme, the peripheral region B is further divided into a pre-determined partitioning number of peripheral k-space portions B1 . . . Bn. Here, in an embodiment, the starting points of the peripheral region B may be assigned according to sorting criteria, for example increasing radial distance as a primary sort key and increasing azimuthal angle, which is measured counterclockwise from the ky-direction, as secondary sort key. The points on the resulting sorted list are then sequentially assigned to one of n disjoint and nonoverlapping subsets forming the peripheral k-space portions Bi, i=1, 2 . . . , n. The Bi have at least approximately equal size.

In FIG. 3, exemplarily a partitioning number n of three is illustrated, wherein the squares belong to B1, the unfilled circles to B2 and the triangles to B3.

Figure 4:
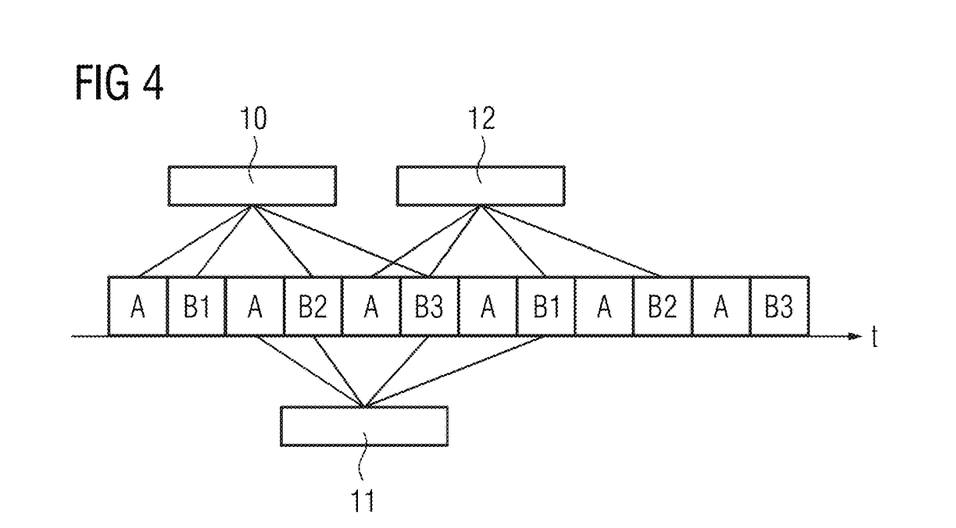

In a step S2, magnetic resonance signals are acquired by parallel imaging using multiple reception coils, for which a three-dimensional sensitivity distribution is known as sensitivity information. The sampling scheme of the k-space 1 is to scan pairs of the central region A and a peripheral k-space portion Bi in a pre-determined order, for example (A, B1), (A, B2), (A, B3), (A, B1), (A, B2), . . . in the example provided above, as also shown in FIG. 4. Each pair thus has two acquisition steps, one for the central region A and one for the respective peripheral k-space portion Bi.

Figure 5:
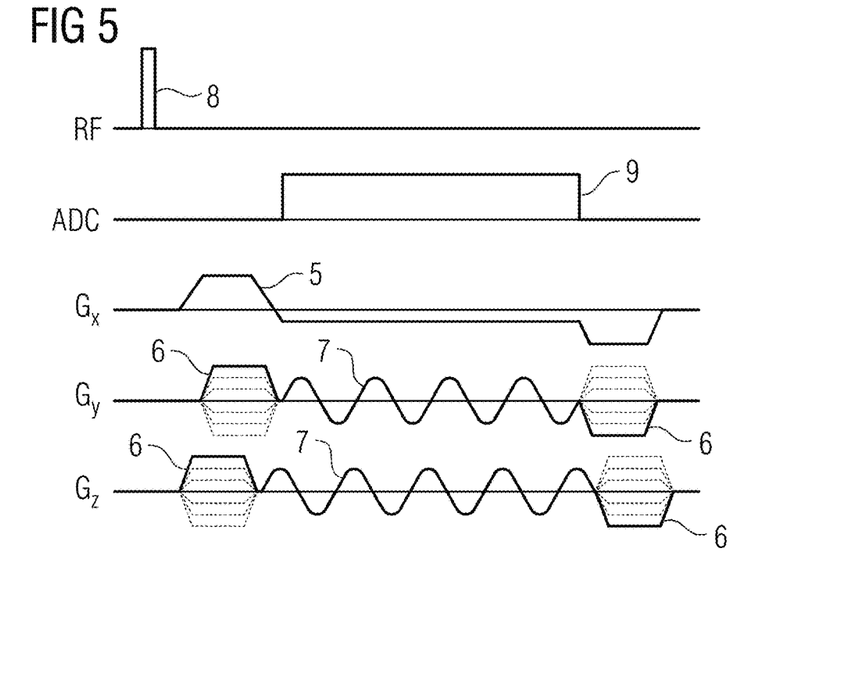

However, step S2 does not use Cartesian trajectories, that is, k-space lines as sub-trajectories associated with each of the points in FIG. 2, but three-dimensional corkscrew trajectories. These are implemented using a wave-encoded 3D gradient echo sequence as exemplarily shown in the pulse diagram of FIG. 5. As can be seen, the usual readout gradient pulses 5 and phase encoding pulses 6 remain unchanged regarding conventional sequences relating to a k-space line, however, additional sinusoidal gradient pulses 7 with a quarter cycle phase shift were added in the phase encoding directions (Gy/Gz). Also indicated in FIG. 5 are the radio frequency pulse 8 and the readout time window 9.

The additional wave-encoding leads to wide voxel-spreading of aliased image voxels in all three spatial dimensions. Therefore, the removal of undersampling artifacts during reconstruction is improved, the resulting g-factor is lower and therefore, reconstructed magnetic resonance images exhibit lower noise enhancement. For example, 2D-CAIPIRINHA undersampling can be employed.

In a step S3 of FIG. 1, a time series of magnetic resonance images, each associated with a time step (TWIST phase), is reconstructed as the magnetic resonance data set. As shown in FIG. 4, a sliding reconstruction window is used. For example, if a first magnetic resonance image 10 is reconstructed from the first shown acquired magnetic resonance signals of B1, B2, and the pair A, B3, for the magnetic resonance image 11 next in time, the older acquisitions of A and B1 are removed and replaced by the magnetic resonance signals of A and B1 acquired next in time. For the next time step, old acquisitions of A and B2 are replaced with the next later acquired magnetic resonance signals of A and B2 for the magnetic resonance image 12, and so on.

It is noted that, in some embodiments, a complete sampling of the k-space 1 (A and all Bi) may be performed at the beginning and/or the end of the acquisition process, such that an initial and/or final reconstruction can be performed, and, for the first n pairs, magnetic resonance signals of the initial complete sampling are successively replaced until the sliding reconstruction window can be employed.

The actual reconstruction in step S3 is performed using a reconstruction technique. Since aliasing is controlled in all three dimensions, the full three-dimensional coil sensitivity distribution is used as the sensitivity information during reconstruction, increasing the amount of total information used.

In this embodiment, an L+S reconstruction technique is combined with the wave-encoded 3D gradient echo trajectory. As already explained, such a compressed sensing model with temporal regularization is particularly advantageous in this case. Consecutive magnetic resonance images 10, 11, 12 differ only marginally and therefore are highly correlated in the temporal dimension. These correlations are exploited to yield high quality reconstructions using the L+S compressed sensing model. Additionally, the controlled aliasing in three dimensions for the case of wave-encoded sampling, lead to higher reconstruction quality. The combination of the wave-encoding technique and the L+S reconstruction technique in particular allows higher acceleration and hence potential for significant progress in temporal resolution, while maintaining high spatial resolution.

Figure 6:
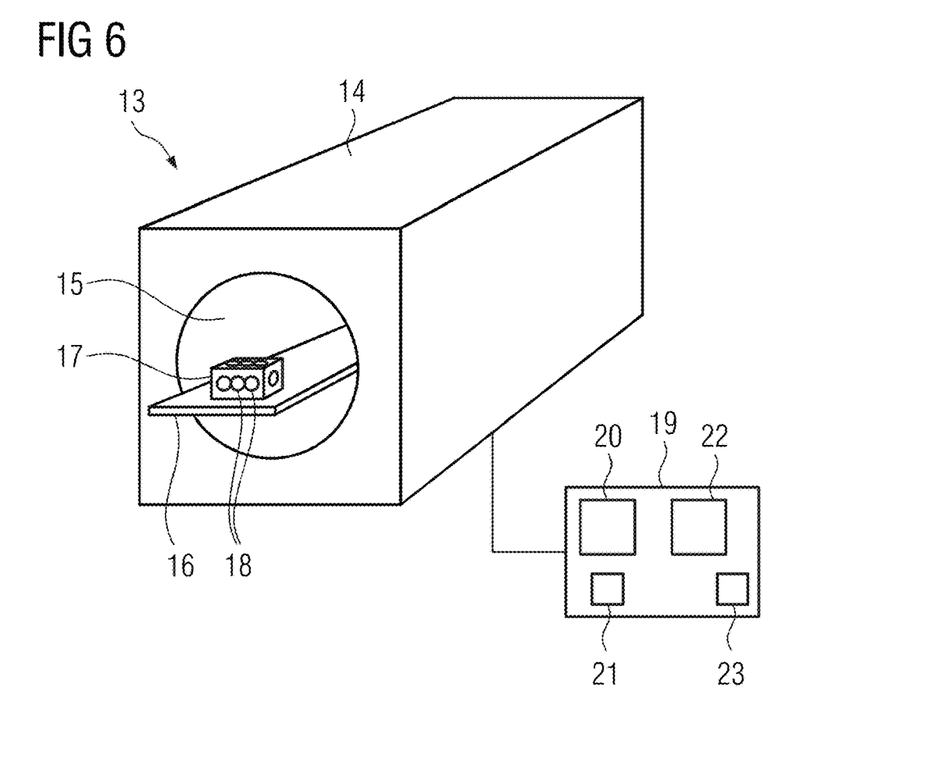

FIG. 6 is a principle drawing of a magnetic resonance imaging device 13 according to one or more example embodiments of the present invention. The magnetic resonance imaging device 13 comprises a main magnet unit 14 having a cylindrical bore 15 into which a patient may be introduced using a patient table 16. Surrounding the bore 15, a radio frequency coil arrangement of a radio frequency system and a gradient coil arrangement of a gradient system (not shown) may be provided. In this case, the magnetic resonance signals are acquired using a local head coil 17 comprising a plurality of reception coils 18 whose three-dimensional coil sensitivity distribution is known as sensitivity information to be used in reconstruction step S3, as explained above.

The operation of the magnetic resonance imaging device 13 is controlled by a control device 19, which comprises a sequence unit 20 for controlling the acquisition of magnetic resonance signals, in particular also according to step S2, a planning unit 21, where step S1 can be executed, and a reconstruction unit 22 for reconstructing magnetic resonance images 10, 11, 12 from the acquired magnetic resonance signals, in particular also according to step S3 as explained above. The control device 19 further comprises a storage device (or, alternatively, means) 23, where, for example, the sensitivity information, acquisition parameters like the division of the k-space 1, magnetic resonance images 10, 11, 12 and the like may be stored.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

Although the present invention has been described in detail with reference to the preferred embodiment, the present invention is not limited by the disclosed examples from which the skilled person is able to derive other variations without departing from the scope of the present invention.

What is claimed is:

1. A computer-implemented method for determining a dynamic contrast-enhanced magnetic resonance data set of an imaging region of a patient, wherein a k-space to be acquired is divided into a central region including a k-space center and a peripheral region surrounding the central region, and wherein the peripheral region includes a partitioning number of peripheral k-space portions, wherein the method comprises:
  acquiring, using a plurality of reception coils, magnetic resonance signals via parallel imaging and a k-space acquisition scheme, in which the central region and one of the peripheral k-space portions are alternatingly imaged in a pair of acquisition steps, such that, after the partitioning number of such pairs, the k-space to be acquired has been imaged and a sliding reconstruction window is applied to reconstruct an additional magnetic resonance image after each pair of acquisition steps, wherein undersampling in at least two k-space directions is performed during acquisition of the k-space, and wherein the peripheral k-space portions are chosen in order; and
  reconstructing a time series of magnetic resonance images forming the dynamic contrast-enhanced magnetic resonance data set from the magnetic resonance signals and sensitivity information regarding the plurality of reception coils by using the sliding reconstruction window and a reconstruction technique for undersampled magnetic resonance data, wherein
    k-space trajectories for each acquisition step are chosen to allow controlled aliasing in all three spatial dimensions including a readout direction,
    for each acquisition step, a k-space trajectory is defined by a wave-encoded 3D gradient echo magnetic resonance sequence using sinusoidal gradient pulses with a quarter cycle phase shift in phase encoding directions,
    a low rank plus sparse reconstruction technique is used as the reconstruction technique, and
    the contrast-enhanced dynamic magnetic resonance data as a space-time matrix is assumed as a linear superposition of a spatially and temporally correlated image background matrix and a sparse dynamic information matrix.

2. The computer-implemented method of claim 1, wherein a TWIST sampling scheme is used to stochastically define the peripheral k-space portions.

3. The computer-implemented method of claim 2, wherein the sensitivity information includes a three-dimensional sensitivity distribution of the plurality of reception coils.

4. The computer-implemented method of claim 2, wherein a gradient system transfer function is used to correct for inaccuracies during reconstruction.

5. The computer-implemented method of claim 1, wherein the sensitivity information includes a three-dimensional sensitivity distribution of the plurality of reception coils.

6. The computer-implemented method of claim 5, wherein a gradient system transfer function is used to correct for inaccuracies during reconstruction.

7. The computer-implemented method of claim 1, wherein a gradient system transfer function is used to correct for inaccuracies during reconstruction.

8. The computer-implemented method of claim 1, wherein the low rank plus sparse reconstruction technique provides a synergistic effect with an incoherent aliasing pattern introduced by the wave-encoded 3D gradient echo magnetic resonance sequence.

9. A magnetic resonance imaging device, comprising a control device configured to perform the computer-implemented method of claim 1.

10. A non-transitory computer-readable storage medium storing computer-executable instructions that, when executed by at least one processor at a control device of a magnetic resonance imaging device, cause the magnetic resonance imaging device to perform the computer-implemented method of claim 1.

11. A control device for a magnetic resonance imaging device, the control device determining a dynamic contrast-enhanced magnetic resonance data set of an imaging region of a patient, wherein a k-space to be acquired is divided into a central region including a k-space center and a peripheral region surrounding the central region, and wherein the peripheral region includes a partitioning number of peripheral k-space portions, wherein the control device comprises:
  processing circuitry configured to cause the control device to
    acquire, using a plurality of reception coils, magnetic resonance signals via parallel imaging and a k-space acquisition scheme, in which the central region and one of the peripheral k-space portions are alternatingly imaged in a pair of acquisition steps, such that, after the partitioning number of such pairs, the k-space to be acquired has been imaged and a sliding reconstruction window is applied to reconstruct an additional magnetic resonance image after each pair of acquisition steps, wherein undersampling in at least two k-space directions is performed during acquisition of the k-space, and wherein the peripheral k-space portions are chosen in order, and reconstruct a time series of magnetic resonance images forming the dynamic contrast-enhanced magnetic resonance data set from the magnetic resonance signals and sensitivity information regarding the plurality of reception coils by using the sliding reconstruction window and a reconstruction technique for undersampled magnetic resonance data, wherein k-space trajectories for each acquisition step are chosen to allow controlled aliasing in all three spatial dimensions including a readout direction, for each acquisition step, a k-space trajectory is defined by a wave-encoded 3D gradient echo magnetic resonance sequence using sinusoidal gradient pulses with a quarter cycle phase shift in phase encoding directions, a low rank plus sparse reconstruction technique is used as the reconstruction technique, and the contrast-enhanced dynamic magnetic resonance data as a space-time matrix is assumed as a linear superposition of a spatially and temporally correlated image background matrix and a sparse dynamic information matrix.

12. A magnetic resonance imaging device comprising:
a radio frequency coil arrangement;
a gradient system; and
the control device of claim 11 to control the magnetic resonance imaging device.

13. The control device of claim 11, wherein the low rank plus sparse reconstruction technique provides a synergistic effect with an incoherent aliasing pattern introduced by the wave-encoded 3D gradient echo magnetic resonance sequence.

* * * * *